(12) United States Patent
Manetakis

(10) Patent No.: US 7,141,056 B2
(45) Date of Patent: Nov. 28, 2006

(54) MULTIPLIER EXTENSION ARRANGEMENT

(75) Inventor: Emmanuel Manetakis, Burlington, MA (US)

(73) Assignee: Microline Pentax Inc., Beverly, MA (US)

( * ) Notice: Subject to any disclaimer, the term of this patent is extended or adjusted under 35 U.S.C. 154(b) by 682 days.

(21) Appl. No.: 10/253,743

(22) Filed: Sep. 24, 2002

(65) Prior Publication Data

US 2003/0023249 A1 Jan. 30, 2003

Related U.S. Application Data

(63) Continuation-in-part of application No. 10/158,726, filed on May 30, 2002, now Pat. No. 6,911,033, which is a continuation-in-part of application No. 10/085,737, filed on Feb. 28, 2002, now Pat. No. 6,840,945, which is a continuation-in-part of application No. 09/934,378, filed on Aug. 21, 2001, now Pat. No. 6,569,171, which is a continuation-in-part of application No. 09/795,808, filed on Feb. 28, 2001, now Pat. No. 6,620,184.

(51) Int. Cl.
*A61B 17/10* (2006.01)

(52) U.S. Cl. .................. 606/142; 606/139; 606/143

(58) Field of Classification Search ............. 606/139, 606/142, 143, 205, 175, 184, 185; 227/175.1, 227/176.1; 74/110, 829
See application file for complete search history.

(56) References Cited

U.S. PATENT DOCUMENTS

| | | | |
|---|---|---|---|
| 3,638,847 A | 2/1972 | Noiles et al. | |
| 4,416,278 A * | 11/1983 | Miller | 606/184 |
| 4,522,207 A | 6/1985 | Klieman et al. | |
| 4,674,504 A | 6/1987 | Klieman et al. | |
| 4,892,244 A | 1/1990 | Fox et al. | |
| 5,174,300 A | 12/1992 | Bales et al. | |
| 5,246,450 A | 9/1993 | Thornton et al. | |
| 5,251,502 A * | 10/1993 | Eisbrenner et al. | 74/110 |
| 5,403,327 A * | 4/1995 | Thornton et al. | 606/143 |
| 5,483,952 A | 1/1996 | Aranyi | |
| 5,607,436 A | 3/1997 | Pratt et al. | |
| 5,626,585 A | 5/1997 | Mittelstadt et al. | |
| 5,626,608 A | 5/1997 | Cuny et al. | |
| 5,772,673 A | 6/1998 | Cuny et al. | |
| 5,951,577 A | 9/1999 | Mayenberger et al. | |
| RE36,720 E | 5/2000 | Green et al. | |
| 6,059,799 A | 5/2000 | Aranyi et al. | |
| 6,277,131 B1 | 8/2001 | Kalikow | |
| 6,306,149 B1 | 10/2001 | Meade | |
| 6,599,298 B1 | 7/2003 | Forster et al. | |
| 6,962,592 B1 * | 11/2005 | Gatturna et al. | 606/184 |

* cited by examiner

*Primary Examiner*—Julian W. Woo
(74) *Attorney, Agent, or Firm*—Greenblum & Bernstein, P.L.C.

(57) ABSTRACT

An elongated medical clip applying device having a handle grip assembly on a proximal end thereof and an elongated channel with a pair of squeezable jaws on a distal end thereof. A push rod arrangement is included having a distal end and a proximal end. The push rod arrangement is utilized for advancing a plurality of clips in a sequential manner between the jaws. The push rod includes a multiplier extender arrangement to increase the distance of travel of the distal end of the push rod arrangement a multiple of the distance of travel of the proximal or input end of the push rod arrangement.

17 Claims, 7 Drawing Sheets

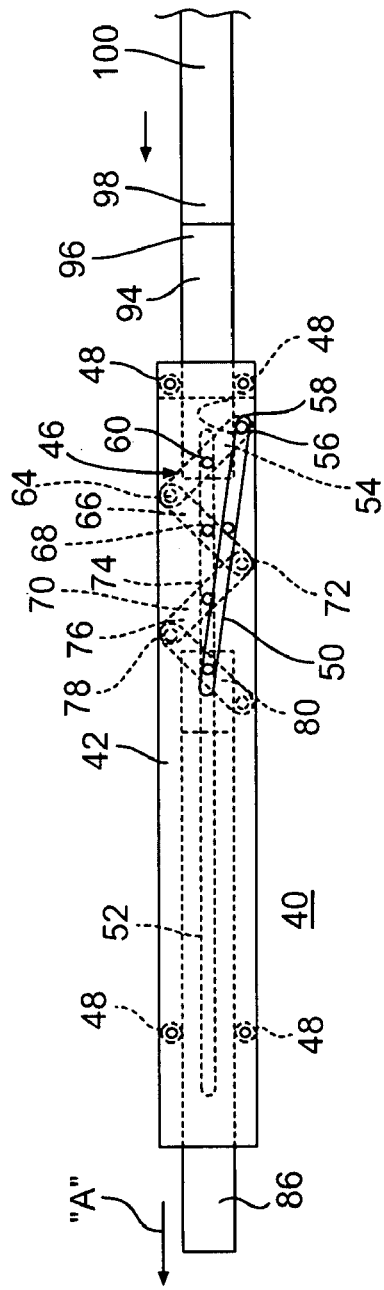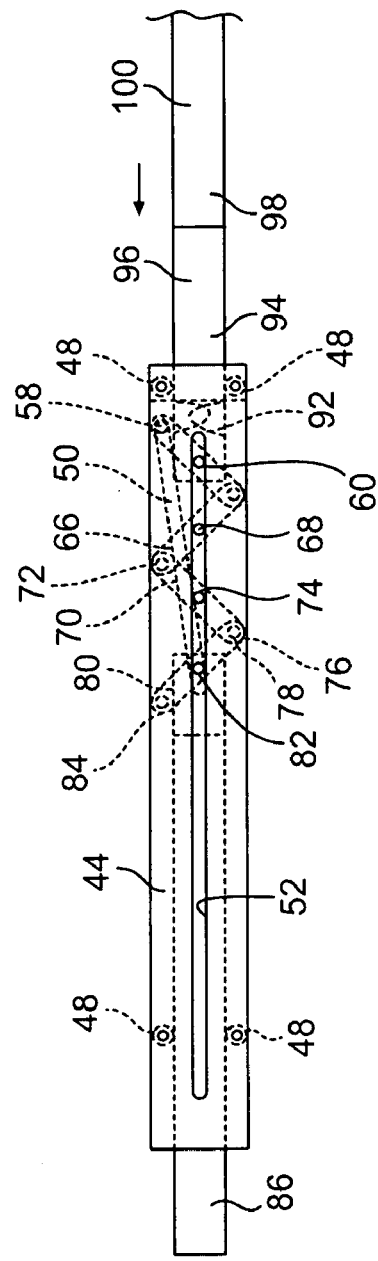

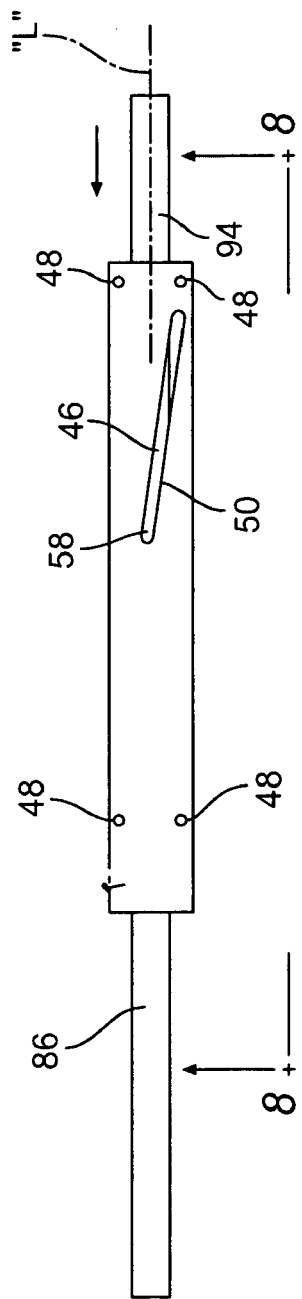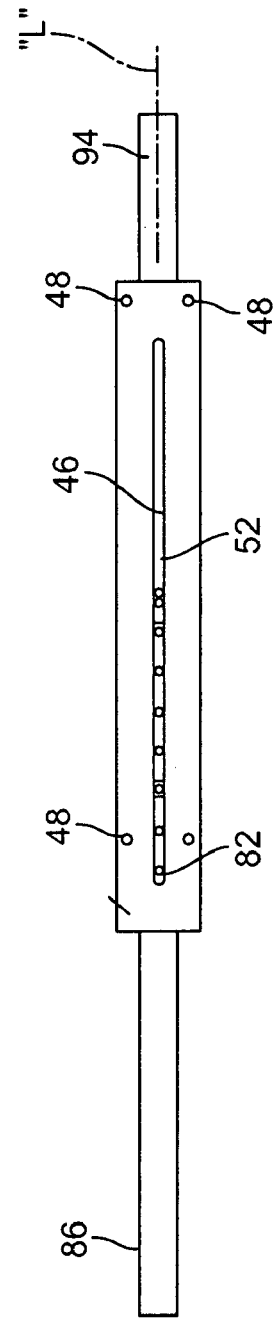

MULTIPLIER EXTENSION ARRANGEMENT

This application is a continuation-in-part application of U.S. patent application Ser. No. 10/158,726 filed 30 May 2002 now U.S. Pat. No. 6,911,033 entitled "Medical Clip Applying Device" which is a continuation-in-part of U.S. patent application Ser. No. 10/085,737 entitled "Medical Clip Applier Safety Arrangement" filed 28 Feb. 2002 which issued as U.S. Pat. No. 6,840,945, which is a continuation-in-part application of U.S. patent application Ser. No. 09/934,378 entitled "Safety Locking Mechanism for a Medical Clip Device" filed 21 Aug. 2001, which issued as U.S. Pat. No. 6,569,171, which is a continuation-in-part of U.S. patent application Ser. No. 09/795,808 entitled "Release Mechanism for Grasping Device" filed 28 Feb. 2001 which issued as U.S. Pat. No. 6,620,184, all of which are incorporated herein by reference, in their entirety.

BACKGROUND OF THE INVENTION

1. Field of the Invention

This invention relates to a plurality of articulable links to extend the capable distance of movement of components of a medical device.

2. Prior Art

Typical modem surgery may be identified as laparoscopic surgery, which may be defined as minimally invasive surgery upon a patient utilizing small or miniaturized medical devices by which body tissue is cut, removed or cauterized by small manipulable devices through small incisions or openings within the patient's body. A grasper or dissector is one such tool for that type of surgery. Such a device may be utilized to grab, dissect, treat or move tissue out of the surgical situs where other tissue may be surgically treated.

Such devices may be seen in the aforementioned U.S. Pat. No. 6,277,131 to Kalikow and U.S. Pat. No. 6,306,149 to Meade. These devices have a handle assembly into which an elongated tubular housing is attached. The elongated housing has a distalmost end with a set of pinching jaws thereon. The pinching jaws in this example are utilized to crimp a clip so as to crimp a mammalian tissue. The jaws are activated by squeezing a trigger on the housing assembly on the proximal end of the device. Such a squeezing trigger motion effects the pinching of the jaws together on a staple-like clip. Should it be desired to utilize a longer legged clip to be pinched within the jaws of that crimping device, longer legged staples would jam such a mechanism and the jaws unfortunately would likely not be able to tolerate such a pinching or squeezing effect.

It is an object of the present invention to provide a multiplier extension arrangement on a medical device to permit that medical device to have a longer reach or extendibility thereof.

It is a further object of the present invention to provide a multiplier extension arrangement which permits a first or forward motion to be converted into a larger second or forward motion and a first or rearward or proximal motion to be converted into a larger rearward or proximal motion relative to an output end of the multiplier extension apparatus.

It is a further object of the present invention to provide an arrangement for permitting longer legged staples or clips to be utilized in a standard triggered-housing assembly of a clip applying device.

It is a further object of the present invention to provide a gain of displacement or distance in a linear tool of a given length, to permit a short-distance traveling bearing to advance a longer legged clip or staple.

It is an object of the present invention to permit the use of the proximal handle (and bearing arrangement) of a "regular" clip applier device with a replacement barrel and clinch jaw arrangement including an extender arrangement to permit larger clips to be properly utilized with that regular clip applier device without having to purchase an entirely new applier device.

It is still yet a further object of the present invention to overcome the disadvantages of the prior art.

BRIEF SUMMARY OF THE INVENTION

The present invention comprises a hand manipulable clip applying device for applying medical tissue pinching clips to mammalian tissue. The clip applying device has a patient engaging distalmost end with a pair of squeezable jaws arranged on the distal end of an elongated channel or frame. The elongated channel is surrounded by an elongated tubular barrel-like enclosure which elongated tube and elongated channel are secured at their respective proximal most ends to the distal end of a pistol-like handle grip assembly. The handle grip assembly includes an arcuately moveable, squeezable trigger. By squeezing the trigger towards a housing portion of the handle grip assembly, a clip is advanced through the elongated channel and into the jaws of the elongated ladder like clip supply cartridge disposed through the elongated housing. The actual sequence comprises the squeezing of the trigger to close the jaws and thus crimp the clip between the jaws, then releasing the trigger to advance a new clip into location between the jaws awaiting the next squeezing of the trigger. The elongated clip supply cartridge is fed into a receiving slot or port in the proximal end of the handle grip assembly.

A rotatable enclosure barrel is rotatably supported within the handle grip assembly. The rotatable enclosure barrel is connected to the proximal end of the elongated channel.

An elongated pusher rod extends adjacent to the lower side of the elongated channel. The elongated pusher rod has a proximal end connected to a proximal bearing surrounding the enclosure barrel at the proximal end of the handle grip assembly. The pusher rod has a distalmost end with a distalmost clip engaging finger arrangement extending from one side thereof. The distalmost clip engaging finger arrangement is movable with respect to the clip loaded cartridge disposed within the elongated channel. Movement of the pusher rod thus effects clips or staples being advanced between the jaws at the distalmost end of the channel.

In the present invention, a multiplier extension arrangement is secured to the lowermost side of the channel at a proximal portion thereat, within the elongated barrel. The multiplier extension arrangement comprises a first elongated plate and a second elongated plate. The first and the second elongated plates sandwich between them an articulable link member arrangement comprising a plurality of connected link members. The link members are longitudinally and pivotably movable between the first plate and the second plate. The first and second plates are separated from one another by spacers arranged at their respective corners. The second elongated plate is secured to the underside of the channel. The first elongated plate has a diagonal cam slot arranged therethrough, running at an angle of about 4 to 10 degrees, and preferably 7 degrees with respect to the longitudinal axis of the multiplier extension arrangement. The elongated second plate has a horizontal cam slot arranged therethrough that runs parallel with respect to the longitudinal axis of the multiplier extension arrangement.

The link members of the link member arrangement comprises a proximal most first link having a first end with a diagonal guide pin extending from one side thereof. The diagonal guide pin of the first or proximal link is arranged to slide within the diagonal cam slot in the elongated first plate. The first link has a horizontal guide pin extending from the other side of the first link and into the horizontal cam slot in the elongated second plate thereadjacent. The diagonal guide pin extends from the proximal end of the first link and out through the elongated second plate in a diagonal slot therein. The first link has a second or distal end which is attached by a hinge to a second link member. The second link member has a horizontal guide pin extending from one side thereof from a midpoint of the second link member into the horizontal cam slot. The distal end of second link member is attached to a third link member by a hinge arranged therebetween. The third link member has a horizontal guide pin extending from a midpoint thereof through the horizontal cam slot on the elongated second plate. The third link member has a distalmost end which is attached by a hinge to a fourth link member. The fourth link member has a horizontal guide pin extending from a midpoint thereof into the horizontal cam slot on the elongated second plate. The horizontal guide pin on the fourth or distalmost link member is also attached to the proximalmost end of a distal multiplier arm. All horizontal guide pins extend from a midpoint of their respective links. The distal multiplier arm is longitudinally displacable between the elongated first plate and the elongated second plate. The distal end of the distal multiplier arm is attached to the proximal end of the distal push rod secured to the lowermost side of the channel of the clip applying device to which the multiplier extension arrangement is attached. The horizontal guide pin extending from the midpoint of the first or proximal most link member is secured to the distalmost end of the proximal multiplier arm. The proximal end of the proximal multiplier arm is attached to the distalmost end of the proximal push rod which extends from the handle grip assembly and which is movable pushed (and pulled) therefrom.

The proximal push rod is moved longitudinally in correspondence to the squeezing and releasing of the trigger relative to the housing of the handle grip assembly.

Longitudinal distal movement of the proximal push rod effects longitudinal distal movement of the proximal multiplier arm. The distal end of the proximal multiplier arm is attached to the first horizontal guide pin pushing that horizontal guide pin distally in the horizontal cam slot within the elongated second plate. A corresponding distal motion is also thus caused in the diagonal guide pin on the proximal end of the first link member which is disposed within the diagonal cam slot on the elongated first plate. Since the diagonal cam slot in the elongated first plate is skewed with respect to the horizontal cam slot in the elongated second plate, a rotational movement is effected in the first link about the horizontal guide pin of the first link member.

Rotational movement of the first link about its respective horizontal guide pin thus effects a rotational movement of the second link member about its respective horizontal guide pin. Rotational movement of the second link member about it horizontal guide pin in the horizontal cam slot thus effects rotational movement of the third link member about its respective horizontal guide pin within the horizontal cam slot. Rotational movement of the third link member about its horizontal guide pin effects motion of the fourth link member about its respective horizontal guide pin situated in the horizontal cam slot. The angular displacement of each of the respective link members and their cammed action within the horizontal cam slot thus effects a longitudinal displacement of the distalmost or fourth link member which, being attached to the proximal end of the distal multiplier arm, effects longitudinal distal displacement thereof. Thus the zig-zag orientation of the connected links are rotated to a straighter alignment to effect to greater overall length of those links, thus effecting the greater length of travel of the distal push rod.

Thus a first distal displacement of the proximal multiplier arm effects a greater longitudinal displacement of the distal multiplier arm (than the dital displacement of the proximal multiplier arm) which thereby effects a greater longitudinal displacement of the push rod supported under the channel and thus effects greater displacement of the staples being pushed by the distalmost end of pushrod.

In the further embodiment of the present invention, a spring may be arranged between the distalmost end of the distal multiplier arm and a portion of the channel. This spring is arranged to provide assistance to the initiation of motion of the distalmost multiplier arm and hence the pushrod, thus helping in its efficiency.

Thus what has been shown is a unique mechanism to permit a first displacement of a pushrod to be multiplied into a first displacement plus a supplemental displacement of a second pushrod downstream from the first pushrod.

Thus what has been shown is a mechanism which permits the use of a common handle trigger assembly to be utilized in conjunction with either a standard or a long legged clip which long legged clip would require longer jaws and longer displacement for entry within those jaws.

The invention thus comprises an elongated medical clip applying device having a handle grip assembly on a proximal end thereof and an elongated channel with a pair of squeezable jaws on a distal end thereof, including a push rod arrangement having a distal end and a proximal end, yhe push rod arrangement utilized for advancing a plurality of clips in a sequential manner between said jaws. The push rod including: a multiplier extender arrangement to increase the distance of travel of the distal end of the push rod arrangement a multiple of the distance of travel of the proximal end of the push rod arrangement. The multiplier extender arrangement may comprise a plurality of connected links cammed between a pair of elongated parallel plates to cam the movement of the links during movement of the proximal end of the push rod arrangement. The elongated plates may comprise a first plate and a second plate spaced parallel and apart from one another by a spacer arrangement, the elongated plates having a longitudinal axis. The first plate may have a cam slot therein arranged at an acute angle with respect to the longitudinal axis of the elongated plates. The second plate may have a horizontal cam slot therein arranged in parallel with the longitudinal axis of the elongated plates. Each of th3e links may have a horizontal guide pin extending therefrom, each of the guide pins being in cammed engagement with the horizontal cam slot. A first of the links may have a diagonal guide pin extending therefrom. The diagonal guide pine may extend into the diagonal slot in the first plate. The multiplier extender arrangement has a proximal multiplier arm in contact with the proximal pusher rod, the multiplier extender arrangement having a distal multiplier arm in contact with the distal pusher rod.

The invention also comprises a method of extending the distance of travel of the distal end of a pushed movable component on a distal end of a frame of a medical device relative to the distance of travel of an input component on a proximal end of the frame, The method may comprise the steps of: connecting a multiplier extender arrangement between the pushed movable component and the input component on the frame of the medical device; arranging a plurality of connected articulated links in the multiplier extender arrangement; pushing the plurality of connected articulated links in a distal direction a first distance by the input component as the links are in a zig-zag orientation; pushing the pushed movable component a second distance, which second distance is greater than the first distance; straightening out the zig-zag orientation of the links as they are moved distally in the extender arrangement; camming the links in an arrangement of slots in a pair of opposed elongated, parallel plates to effect an angular reorientation of the links as they are moved distally to increase their combined overall length; arranging a handle grip assembly to replace a first push rod arrangement thereon having a shorter distal advance capacity; arranging a guide pin in each of the links; and mating the pins in the slots to facilitate said camming of the links with respect to the plates.

The invention also comprises a method of extending the reachable output length of a device where the input length of the device is limited, comprising: moving a first elongated input rod longitudinally a first distance along a longitudinal axis thereof from an input component on a frame of the device and into a multiplier arrangement; moving and output rod longitudinally a second distance along a longitudinal axis thereof from the multiplier arrangement to push a movable component of the device; connecting a multiplier extender arrangement between the pushed movable component and the input component on the frame of the device; arranging a plurality of connected articulated links in the multiplier extender arrangement; pushing the plurality of connected articulated links in a distal direction a first distance by said input component as the links are in a zigzag orientation; pushing the pushed movable component a second distance, which second distance is greater than the first distance; straightening out the zig-zag orientation of the links as they are moved distally in the extender arrangement; camming the links in an arrangement of slots in a pair of opposed elongated, parallel plates to effect an angular re-orientation of the links as they are moved distally to increase their combined overall length to extend the reach of the device.

BRIEF DESCRIPTION OF THE DRAWINGS

The objects and advantages of the present invention will become more apparent when viewed in conjunction with the following drawings in which:

FIG. 4 is a side elevational view of an extension multiplier arrangement constructed according to the principles of the present invention showing a view of the first elongated plate thereof;

FIG. 5 is a side elevational view of the extension multiplier arrangement showing the elongated second plate thereof with the links therebetween shown in phantom;

FIG. 6 is a side elevational view similar to FIG. 4 with the extension multiplier device in full extension, as seen with respect to the elongated first plate;

FIG. 7 is a view similar to FIG. 6 showing the elongated second plate when the extension multiplier device is in its extended state;

DETAILED DESCRIPTION OF THE PREFERRED EMBODIMENTS

Figure 1:
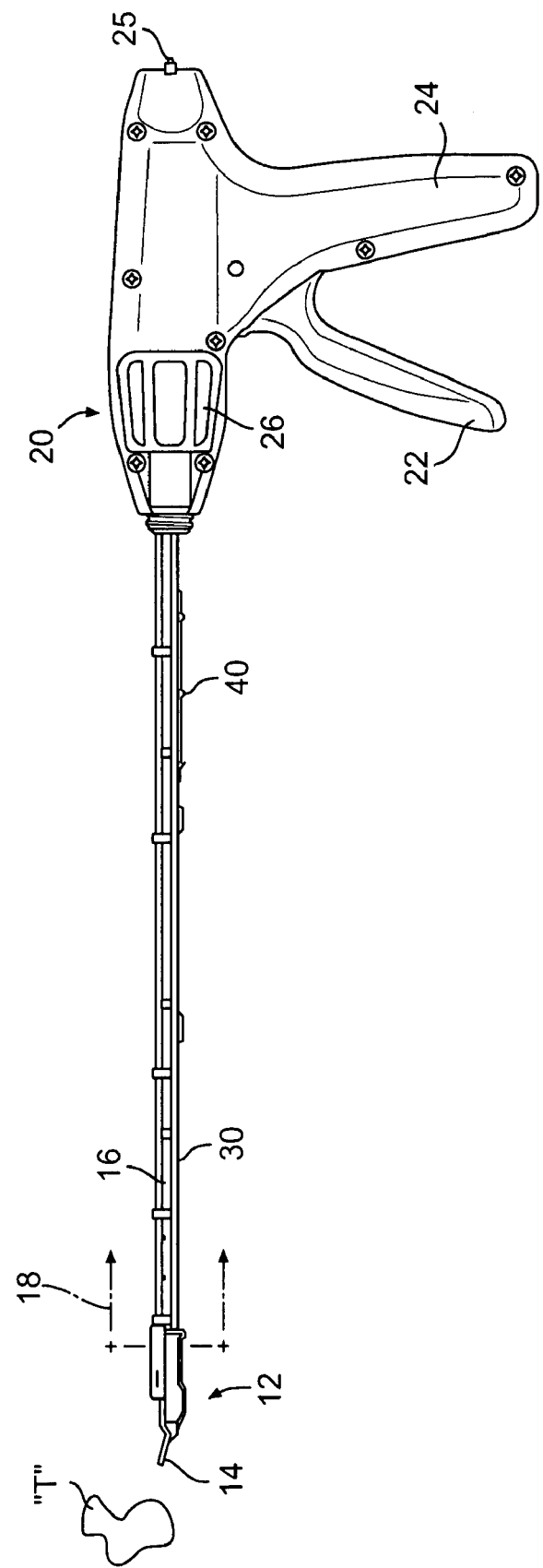
FIG. 1 is a side elevational view of a clip applying device constructed according to the principles of the present invention.

Referring now to the drawings in detail, and particularly to FIG. 1, there is shown the present invention which comprises a hand manipulable clip applying device 10 for applying medical tissue pinching clips to mammalian tissue "T". The clip applying device 10 has a patient engaging distalmost end 12 with a pair of squeezable jaws 14 arranged on the distal end of an elongated channel or frame 16. The elongated channel 16 is normally surrounded by an elongated tubular barrel-like enclosure 18, which elongated tube 18 and elongated channel 16 are secured at their respective proximal most ends to the distal end of a pistol-like handle grip assembly 20. The handle grip assembly 20 includes an arcuately moveable, squeezable trigger 22. By squeezing the trigger 22 towards a housing portion 24 of the handle grip assembly 20, a clip (not shown for clarity) is advanced through the elongated channel 16 and between the jaws 14 distal of an elongated ladder-like clip supply cartridge (not shown for clarity)) disposed through the elongated housing 20. The actual sequence comprises the squeezing of the trigger 22 to close the jaws 14 and thus crimp the clip between the jaws 14 onto a tissue "T", then releasing the trigger 22 to advance a new clip into location between the jaws awaiting the next squeezing of the trigger. The elongated clip supply cartridge is fed into a receiving slot or port 25 in the proximal end of the handle grip assembly 20.

A rotatable enclosure barrel 26 is rotatably supported within the handle grip assembly 20. The rotatable enclosure barrel 26 is connected to the proximal end of the elongated channel 16.

Figure 2:
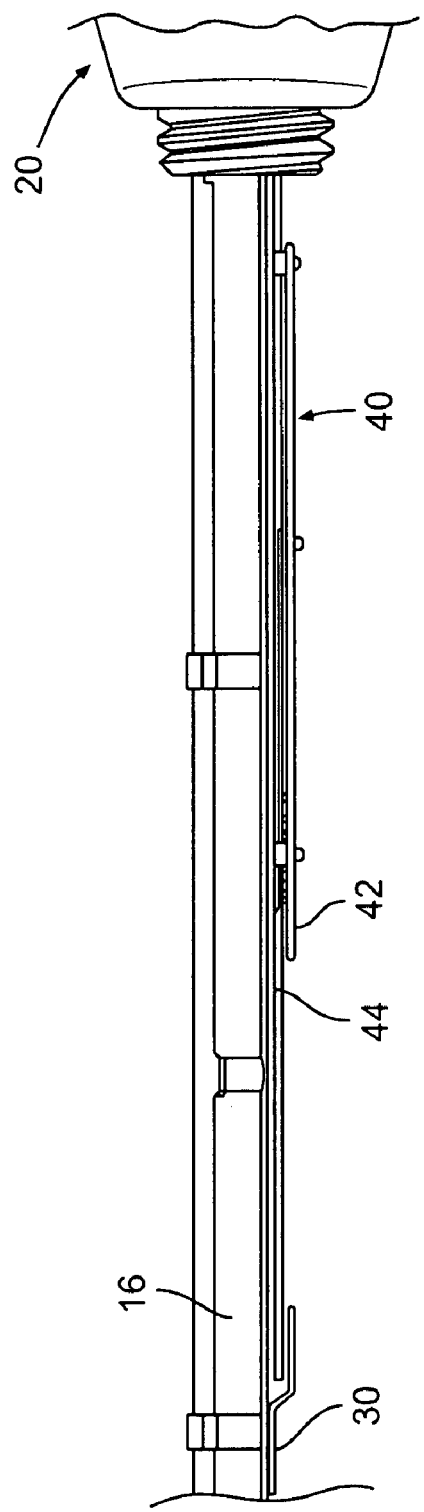
FIG. 2 is a side elevational view of an extension multiplier arrangement attached to a portion of the clip applying device shown in FIG. 1 (without its barrel housing therearound)
Figure 3:
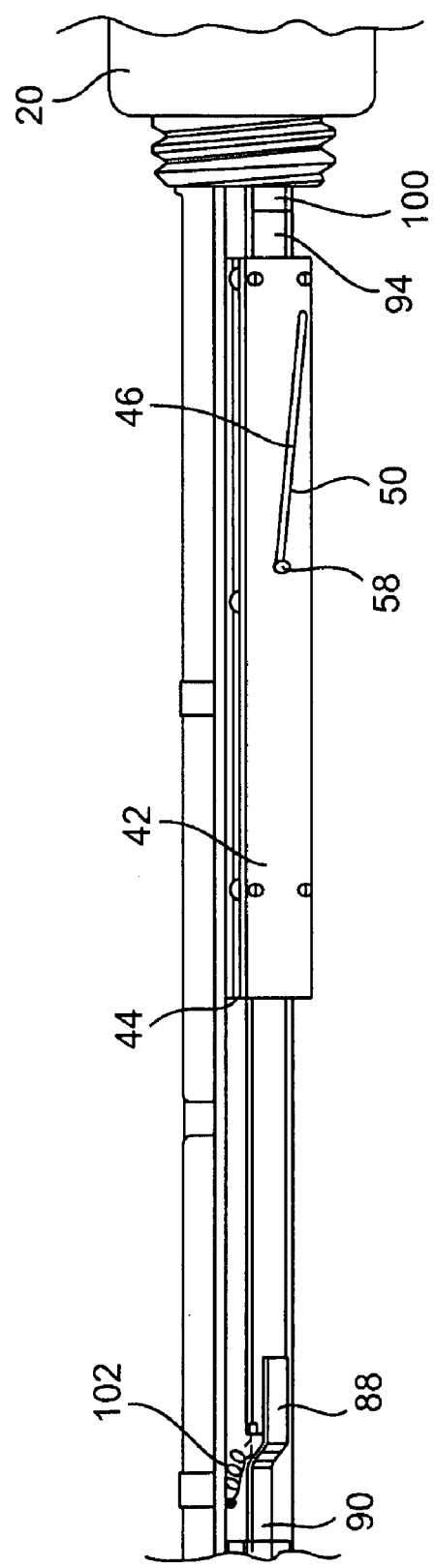
FIG. 3 is a perspective view of the extension multiplier device shown in FIG. 2.
Figure 8:
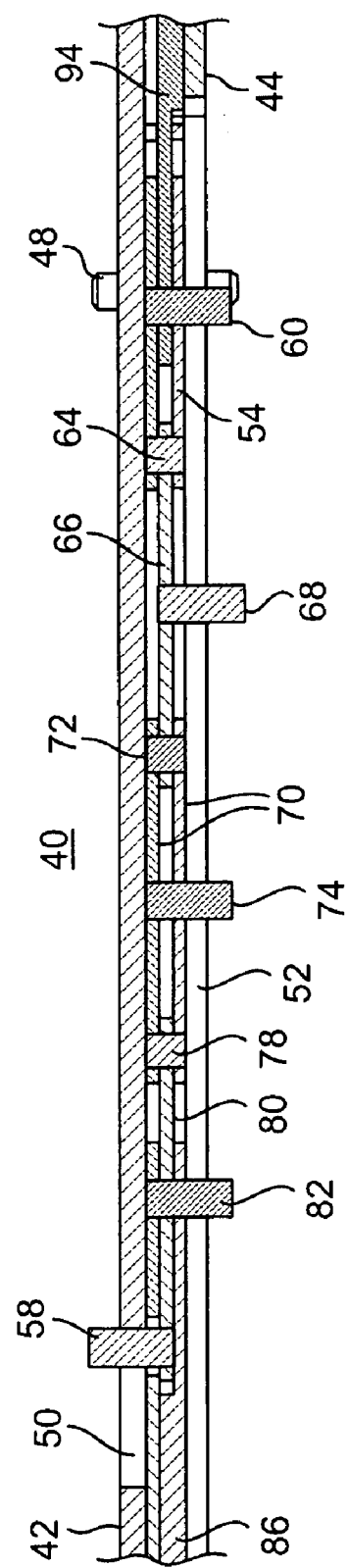
FIG. 8 is a view taken along the lines 8—8 of FIG. 6.

An elongated pusher rod 30 extends adjacent to the lower side of the elongated channel 16, as shown in FIGS. 1, 2 and 3. The elongated pusher rod 30 has a proximal end connected to a proximal bearing within the enclosure barrel 26 at the distal end of the handle grip assembly 20. The pusher rod 30 has a distalmost end with a distalmost clip engaging finger arrangement extending from one side thereof as shown in the recited patents incorporated herein by reference. The distalmost clip engaging finger arrangement is movable with respect to the clip loaded cartridge disposed within the elongated channel 16. Movement of the pusher rod 30 thus effects clips or staples being advanced between the jaws 14 at the distalmost end of the channel 16.

In the present invention, a multiplier extension arrangement 40 is secured to the lowermost side of the channel 16 as shown in FIGS. 1, 2 and 3, at a proximal portion thereat, (normally arranged enclosed within the elongated barrel 18, only a portion of the barrel 18 being shown in phantom, for clarity of viewing). The multiplier extension arrangement 40, as shown more completely in FIGS. 3–8, comprises a first elongated plate 42 and a second elongated plate 44. The first and the second elongated plates 42 and 44 sandwich between them an articulable link member arrangement 46 comprising a plurality of connected link members. The link members are longitudinally and pivotably movable between the first plate 42 and the second plate 44. The first and second plates 42 and 44 are separated from one another by spacers 48 arranged at their respective corners. The second elongated plate 44 is secured to the underside of the channel 16 as may be seen in FIG. 2. The first elongated plate 42 has a diagonal cam slot 50 arranged therethrough, as may be seen in FIGS. 3, 4, 5, 6 and 8, running at an angle of about 4 to 10 degrees (preferably about 7 degrees) with respect to the longitudinal axis "L" of the multiplier extension arrangement 40, as shown in FIG. 6. The elongated second plate 44 has a horizontal cam slot 52 arranged therethrough that runs parallel with respect to the longitudinal axis "L" of the multiplier extension arrangement 40, as may be seen in FIGS. 4, 5, 7 and 8.

Figure 9:
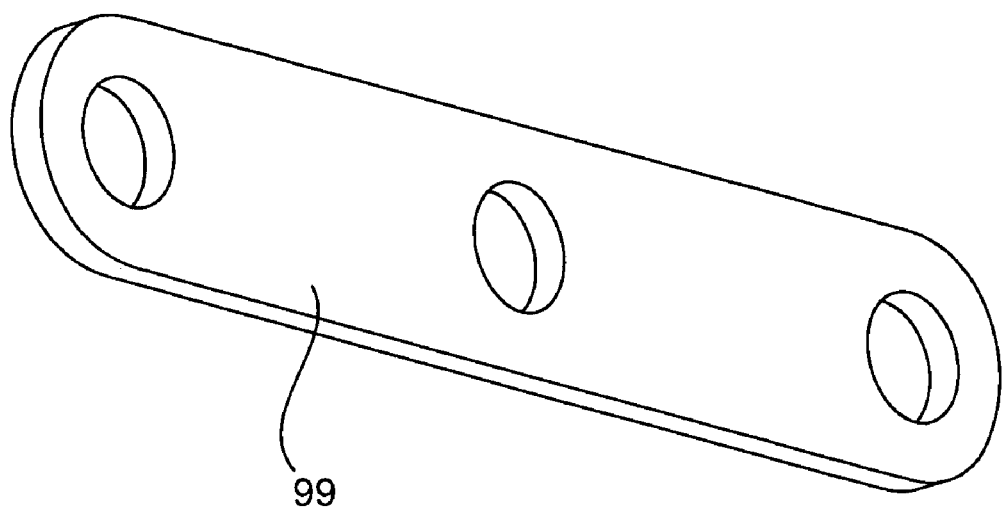
FIG. 9 is a perspective view of one of the link members comprising a portion of the link assembly.

The link members of the link member arrangement 46 comprises a proximal most first link 54 having a first end 56 with a diagonal guide pin 58 extending from one side thereof, as is shown in FIGS. 4, 5 and 6. The link arrangement 46 is shown in a zig-zag configuration in FIGS. 4 and 5, that link arrangement 46 straightening out into a generally straight orientation, as indicated in FIGS. 6 and 7. (A typical link 99 is shown in FIG. 9, which either comprises the link member or one "side" of the link member of a parallel link member arrangement). The diagonal guide pin 58 of the first or proximal link 54 is arranged to slide within the diagonal cam slot 50 in the elongated first plate 42. The first link 54 has a horizontal guide pin 60 extending from the other side of the first link 54 and into the horizontal cam slot 52 in the elongated second plate 44 thereadjacent. The horizontal guide pin 60 extends from the proximal end of the first link 54 and out through the elongated second plate 44. The first link 54 has a second or distal end 62 which is attached by a hinge 64 to a second link member 66. The second link member 66 has a horizontal guide pin 68 extending from one side thereof from a midpoint of the second link member 66 through the elongated second plate 44. The distal end of second link member 66 is attached to a third link 70 member by a hinge 72 arranged therebetween. The third link member 70 has a horizontal guide pin 74 extending from a midpoint thereof through the horizontal cam slot 52 on the elongated second plate 44. The third link member 70 has a distalmost end 76 which is attached by a hinge 78 to a fourth link member 80. The fourth link member 80 has a horizontal guide pin 82 extending from a midpoint thereof into the horizontal cam slot 52 on the elongated second plate 44, as shown in FIGS. 4, 5, 6, 7 and 8. The horizontal guide pin 82 on the fourth or distalmost link member 80 is also attached to the proximalmost end 84 of a distal multiplier arm 86. The distal multiplier arm 86 is longitudinally displacable between the elongated first plate 42 and the elongated second plate 44, as indicated by the arrow "A" in FIG. 4. The distal end of the distal multiplier arm 86 is attached to the proximal end 88 of the distal push rod 90 secured to the lowermost side of the channel 16 of the clip applying device 10 to which the multiplier extension arrangement 40 is attached, as shown in FIG. 3. The horizontal guide pin 60 extending from the midpoint of the first or proximalmost link member 54 is secured to the distalmost end 92 of the proximal multiplier arm 94. The proximal end 96 of the proximal multiplier arm 94 is attached to the distalmost end 98 of the proximal push rod 100 which extends from the handle grip assembly 20, as shown in FIGS. 3, 4 and 5.

The proximal push rod 100 is moved longitudinally in correspondence to the squeezing and releasing of the trigger 22 relative to the housing 24 of the handle grip assembly 20.

Longitudinal distal movement of the proximal push rod 100 effects longitudinal distal movement of the proximal multiplier arm 94. The distal end 92 of the proximal multiplier arm 94 is attached to the first horizontal guide pin 60 pushing that horizontal guide pin 60 distally in the horizontal cam slot 52 within the elongated second plate 44. A corresponding distal motion is also thus caused in the horizontal guide pin 60 on the proximal end of the first link member 54 which is disposed within the horizontal cam slot 52 on the elongated second plate 44. Since the diagonal cam slot 50 in the elongated first plate 42 is skewed with respect to the horizontal cam slot 52 in the elongated second plate 44, a counterwise (as seen in FIG. 4) rotational movement is effected in the first link 54 about the horizontal guide pin 60 of the first link member 54.

Rotational movement of the first link 54 about its respective horizontal guide pin 60 thus effects a rotational movement of the second link member 66 about its respective horizontal guide pin 68. Rotational movement of the second link member 66 about it horizontal guide pin 68 in the horizontal cam slot 52 thus effects rotational movement of the third link 70 member about its respective horizontal guide pin 74 within the horizontal cam slot 52. Rotational movement of the third link member 70 about its horizontal guide pin 74 effects motion of the fourth link member 80 about its respective horizontal guide pin 82 situated in the horizontal cam slot 52. The angular displacement of each of the respective link members 54, 66, 70 and 80 and their cammed action within the horizontal cam slot 52 thus effects a longitudinal displacement of the distalmost or fourth link member 80 which, being attached to the proximal end 84 of the distal multiplier arm 86, effects longitudinal distal displacement thereof.

Thus a first distal displacement of the proximal multiplier arm 94 effects a greater longitudinal displacement of the distal multiplier arm 86 (than the distal displacement of the proximal multiplier arm) which thereby effects a greater longitudinal displacement of the push rod 90 supported under the channel 16, and thus effects greater displacement of the staples being pushed by the distalmost end of pushrod 90.

In the further embodiment of the present invention, a spring 102 may be arranged between the distalmost end of the distal multiplier arm 86 and a downstream portion of the channel 16. This spring 102 is arranged to provide assistance to the initiation of motion of the distalmost multiplier arm 86 and hence the pushrod 90, thus helping in its efficiency.

Thus what has been shown is a unique mechanism to permit a first displacement of a proximal pushrod 100 to be multiplied into a first displacement plus a supplemental displacement of a second pushrod 90 downstream from the first pushrod 100.

Thus what has been shown is a mechanism which permits the use of a common handle trigger assembly to be utilized in conjunction with either a standard or a long legged clip which long legged clip would require longer jaws and longer displacement for entry within those jaws.

I claim:

1. An elongated medical clip applying device having a handle grip assembly on a proximal end thereof and an elongated channel with a pair of squeezable jaws on a distal end thereof, including a push rod arrangement having a distal end and a proximal end, said push rod arrangement utilized for advancing a plurality of clips in a sequential manner between said jaws, said push rod arrangement including:

a multiplier extender arrangement to increase the distance of travel of said distal end of said push rod arrangement a multiple of the distance of travel of said proximal end of said push rod arrangement.

2. The elongated medical clip applying device as recited in claim 1, wherein said multiplier extender arrangement comprises a plurality of connected links cammed between a pair of elongated parallel plates to cam the movement of said links during movement of said proximal end of said push rod arrangement.

3. The elongated medical clip applying device as recited in claim 2, wherein said elongated plates comprise a first plate and a second plate spaced parallel and apart from one another by a spacer arrangement, said elongated plates having a longitudinal axis.

4. The elongated medical clip applying device as recited in claim 3, wherein first plate has a cam slot therein arranged at an acute angle with respect to said longitudinal axis of said elongated plates.

5. The elongated medical clip applying device as recited in claim 4, wherein a first of said links has a diagonal guide pin extending therefrom.

6. The elongated medical clip applying device as recited in claim 5, wherein said diagonal guide pin extends into said diagonal slot in said first plate.

7. The elongated medical clip applying device as recited in claim 3, wherein said second plate has a horizontal cam slot therein arranged in parallel with said longitudinal axis of said elongated plates.

8. The elongated medical clip applying device as recited in claim 7, wherein each of said links have a horizontal guide pin extending therefrom, each of said guide pins being in cammed engagement with said horizontal cam slot.

9. The elongated medical clip applying device as recited in claim 1, wherein said multiplier extender arrangement has a proximal multiplier arm in contact with said proximal pusher rod, said multiplier extender arrangement having a distal multiplier arm in contact with said distal pusher rod.

10. The elongated medical clip applying device as recited in claim 9, wherein a spring is arranged onto said push rod to assist said extender arrangement.

11. A method of extending the distance of travel of the distal end of a pushed movable component on a distal end of a frame of a medical device relative to the distance of travel of an input component on a proximal end of said frame, comprising:
    connecting a multiplier extender arrangement between said pushed movable component and said input component on said frame of said medical device;
    arranging a plurality of connected articulated links in said multiplier extender arrangement;
    pushing said plurality of connected articulated links in a distal direction a first distance by said input component as said links are in a zig-zag orientation;
    pushing said pushed movable component a second distance, which second distance is greater than said first distance; and
    straightening out said zig-zag orientation of said links as they are moved distally in said extender arrangement.

12. The method of claim 11, including:
    camming said links in an arrangement of slots in a pair of opposed elongated, parallel plates to effect an angular re-orientation of said links as they are moved distally to increase their combined overall length.

13. The method of claim 12, including:
    placing said multiplier extender arrangement on a handle grip assembly to replace a first push rod arrangement thereon having a shorter distal advance capacity.

14. The method of claim 12, including:
    arranging a guide pin in each of said links; and
    mating said pins in said slots to facilitate said camming of said links with respect to said plates.

15. A method of extending the reachable output length of a medical device where the input length of said device is limited, comprising:
    connecting a multiplier arrangement between a first elongated input rod and an input component on a frame of said medical device;
    arranging a plurality of connected articulated links in said multiplier arrangement;
    moving said first elongated input rod longitudinally a first distance along a longitudinal axis thereof from said input component and into said multiplier arrangement as said links are in a zig-zag orientation;
    moving an output rod longitudinally a second distance along a longitudinal axis thereof from said multiplier arrangement to push a movable medical tool of said medical device; and
    straightening out said zig-zag orientation of said links as they are moved distally in said multiplier arrangement.

16. A method of extending the reachable output length of a device where the input length of said device is limited, comprising:
    connecting a multiplier extender arrangement between a pushed movable component and an input component on a frame of said device;
    arranging a plurality of connected articulated links in said multiplier extender arrangement;
    pushing said plurality of connected articulated links in a distal direction a first distance by said input component as said links are in a zig-zag orientation;
    pushing said pushed movable component a second distance, which second distance is greater than said first distance and;
    straightening out said zig-zag orientation of said links as they are moved distally in said extender arrangement.

17. The method of claim 16, including:
    camming said links in an arrangement of slots in a pair of opposed elongated, parallel plates to effect an angular re-orientation of said links as they are moved distally to increase their combined overall length to extend the reach of said device.

* * * * *